United States Patent [19]
Kleiman

[11] Patent Number: 5,860,426
[45] Date of Patent: Jan. 19, 1999

[54] CHOLECYSTOSCOPIC CANNULA AND CHOLECYSTOSCOPIC GALLBLADDER LASER-SCLEROSIS PROCEDURE

[76] Inventor: Aldo Sergio Kleiman, Blas Parera St. No. 910, City of Rosario, Province of Santa Fe, Argentina

[21] Appl. No.: 744,527

[22] Filed: Nov. 6, 1996

[51] Int. Cl.$^6$ .................................................... A61B 19/00
[52] U.S. Cl. ................................ 128/898; 604/28; 604/49
[58] Field of Search ................................ 604/49, 28, 73, 604/93, 19; 606/1, 2, 27, 30; 128/898; 600/101

[56] References Cited

U.S. PATENT DOCUMENTS

| | | | |
|---|---|---|---|
| 5,041,124 | 8/1991 | Kensey | 606/170 |
| 5,045,056 | 9/1991 | Behl | 604/49 |
| 5,100,388 | 3/1992 | Behl et al. | 604/113 |
| 5,222,938 | 6/1993 | Behl | 604/49 |
| 5,433,708 | 7/1995 | Nichols et al. | 604/113 |
| 5,542,928 | 8/1996 | Evans et al. | 604/113 |

OTHER PUBLICATIONS

For Reference Only: Greenberger et al. "Harrison's Principle's of Internal Medicine" vol. 2, 13th ed., McGraw–Hill Publishing, Chapter 272, pp. 1504–1516, 1994.

Primary Examiner—Mickey Yu
Assistant Examiner—Kelly O'Hara
Attorney, Agent, or Firm—Sughrue, Mion, Zinn, Macpeak & Seas, PLLC

[57] ABSTRACT

A cholecystoscopic laser-sclerosis surgical procedure for the elimination of a human gallbladder in a single session using a local anesthesia, which utilizes a specially-designed cholecystoscopic cannula to couple the gallbladder fundus to the cannula by forcing a ring of gallbladder tissue into a groove in the cannula, by performing an operative endoscopy inside the gallbladder, closing the cystic duct meatus using a forceps, sealing the cystic duct using electrocoagulation, removing the gallstones, ablating the mucous membrane of the gallbladder by using a $CO_2$ laser, injecting a biological cement into the gallbladder, applying a vacuum in order to collapse the gallbladder, eliminating the gallbladder tissue within the cannula by using a $CO_2$ laser or electrocoagulation, and finally, releasing the coupling of the cannula to the gallbladder fundus and removing the cholecystoscopic cannula. The gallbladder disappears by means of atrophy.

35 Claims, 15 Drawing Sheets

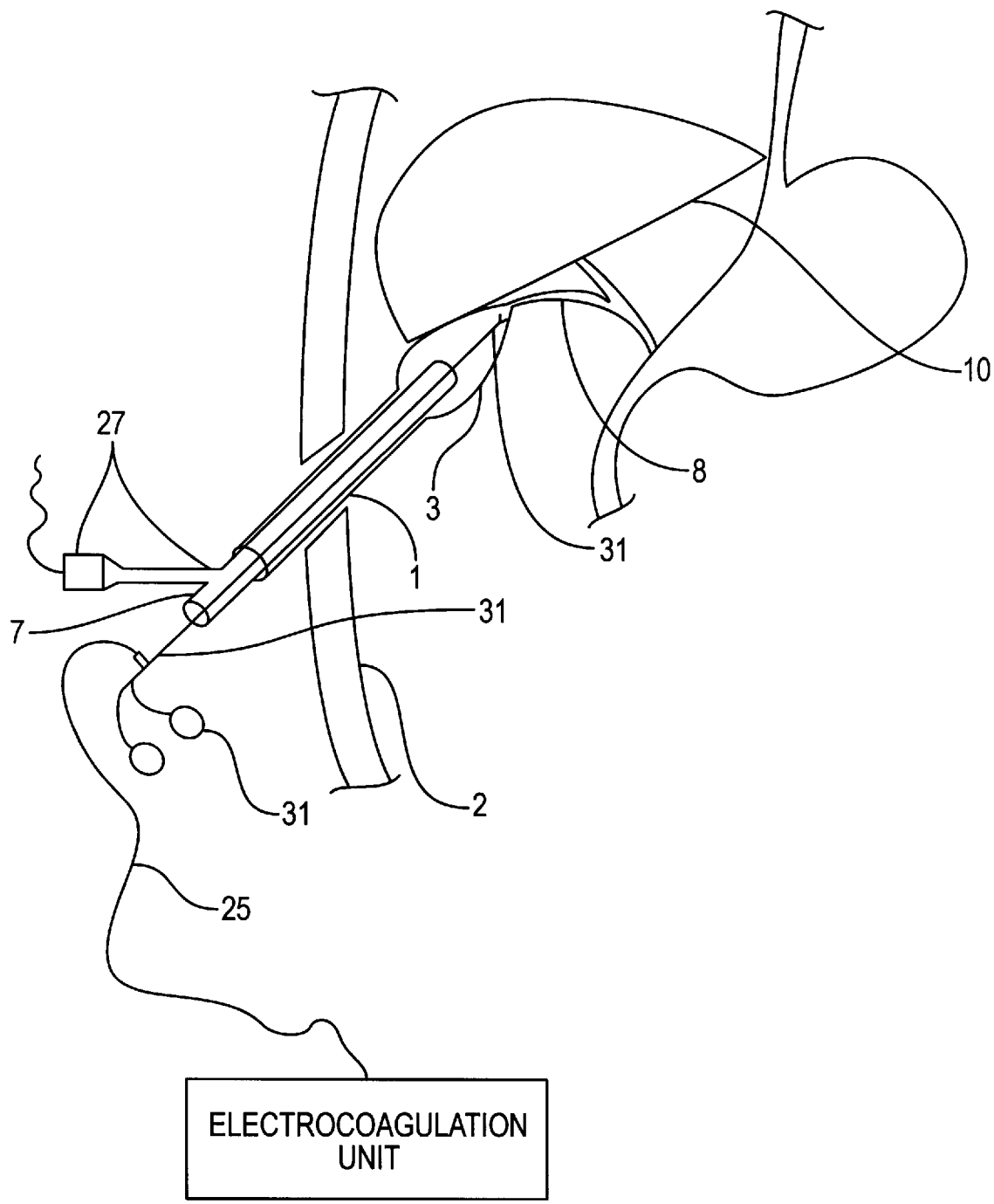

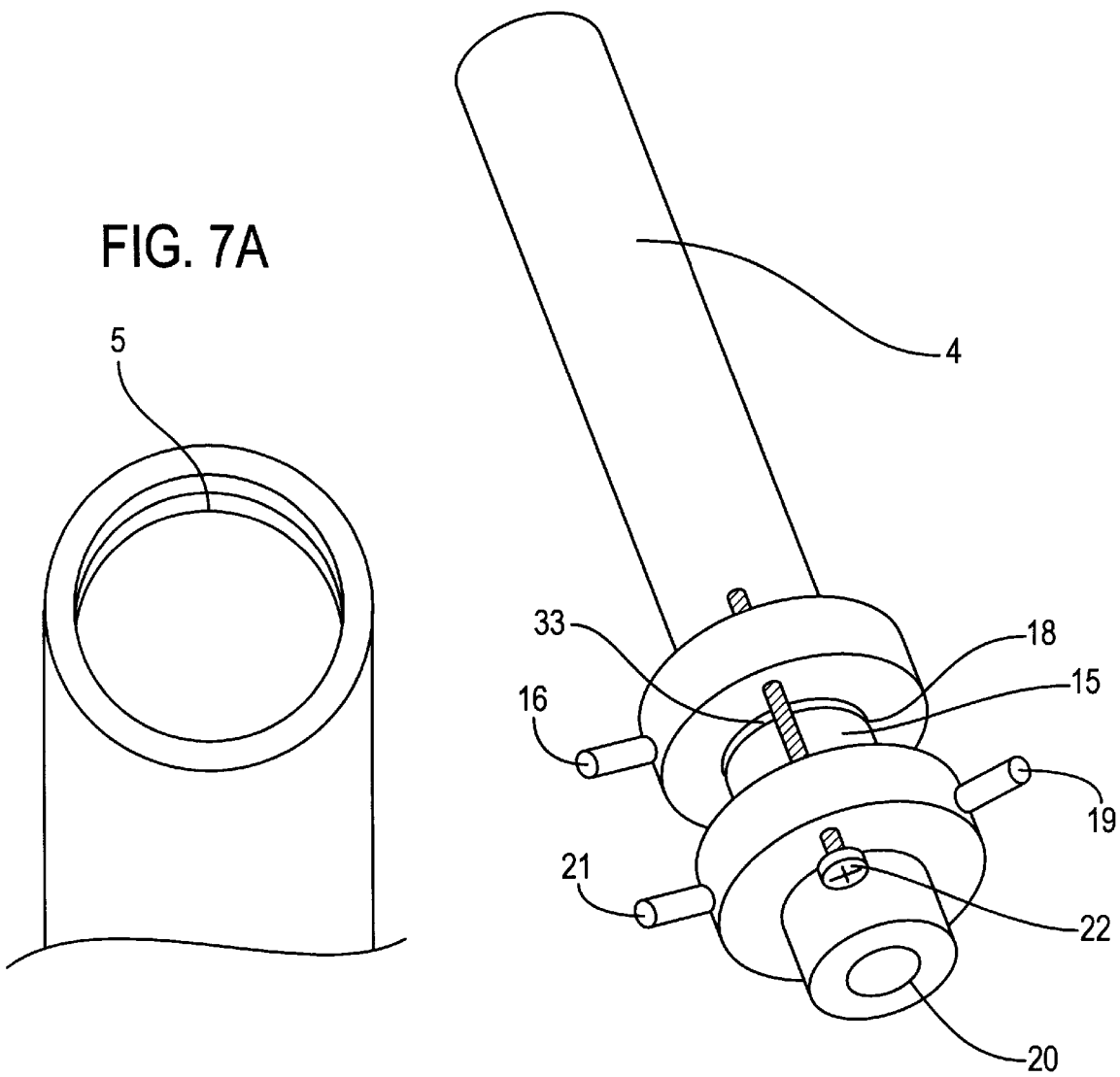

CHOLECYSTOSCOPIC CANNULA AND CHOLECYSTOSCOPIC GALLBLADDER LASER-SCLEROSIS PROCEDURE

BACKGROUND OF THE INVENTION

The present invention relates to a cannula and a procedure for gallbladder elimination.

The accepted medical practice in resolving gallbladder lithiasis is the complete elimination of the gallbladder and its stones. There are two methods in present usage which achieve that goal:

1) the cholecystectomy (removal of the gallbladder) and
2) the percutaneous radioscopic gallbladder chemical-sclerosis (the gallbladder disappears by means of atrophy).

Cholecystectomy, which is a major, accepted and successful surgical procedure (FIG. 1A), is performed by means of an abdominal incision (a laparotomy) or by means of an abdominal endoscopy (laparoscopy). In both cases, general anesthesia is required. The conventional cholecystectomy, which is used most often, requires general anesthesia because of the need to make an incision in the abdominal wall 2 to remove the gallbladder 3 and close the cystic duct 8 (the exit duct from the gallbladder 3 which communicates between the gallbladder 3 and the main duct 9 which leads to the liver 10). The endoscopic (or laparoscopic) cholecystectomy requires general anesthesia also, as the procedure involves a hypertensive pneumoperitoneum, where the abdomen is insufflated to create a space within which the surgeon can work.

Percutaneous radioscopic gallbladder chemical-sclerosis (FIG. 1B) requires only a minor local anesthesia. The procedure commences with a puncture in the abdominal wall 2 by insertion of a needle (not shown) and then a catheter 24 into the gallbladder 3 while under radioscopic control. Dilatation of the passage created by the catheter 24 is performed in a progressive manner over several days. Retrieval of the gallbladder stones 11 is performed by means of instruments placed through the dilated passage under radioscopic control. Occlusion of the cystic duct 8 (the exit duct from the gallbladder 3 which communicates between the gallbladder and the main duct 9 which leads to the liver 10) is performed by means of electrocoagulation using a monopolar wire or bipolar wires guided under radioscopic control. The scar created by the electrocoagulation procedure requires several days to occlude the cystic duct 8. Ablation of the gallbladder mucous membrane (the inner layer of the gallbladder 3) is then performed by means of chemical liquids injected through a catheter 24 into the gallbladder lumen, in repeated sessions over weeks or months. The percutaneous radioscopic gallbladder chemical-sclerosis procedure removes the bile and stones 11, closes the cystic duct 8, and ablates the gallbladder mucous membrane, inducing a definitive sclero-atrophy until the gallbladder 3 disappears. Although this procedure is mini-invasive and requires only local anesthesia, it is used infrequently in high (surgical) risk patients (in whom it is necessary to avoid general anesthesia) as it has the drawback of requiring multiple sessions over weeks or months to be completed.

SUMMARY OF THE INVENTION

The object of the invention is to provide a new procedure which combines the advantages of the percutaneous gallbladder chemical-sclerosis procedure, which is very mini-invasive and utilizes only a local anesthesia, with that of the cholecystectomy which is a single session procedure.

The cholecystoscopic laser-sclerosis surgical procedure for elimination of the gallbladder comprises the steps of inserting a specially-designed cholecystoscopic cannula through a small incision in the abdominal wall and guiding the cannula toward the gallbladder fundus, coupling the cannula to the gallbladder fundus by forcing a ring of tissue of the gallbladder fundus into a groove at the distal end of the cannula by applying a vacuum, perforating the gallbladder wall at the gallbladder fundus and performing an operative endoscopy inside the gallbladder, applying a local anesthetic into the peritoneal area between the gallbladder and the liver, closing the cystic duct meatus using a forceps and sealing it using electrocoagulation, removing the gallstones from the gallbladder using lithotritor forceps, ablating the mucous membrane of the gallbladder by using a $CO_2$ laser, injecting a biological cement into the gallbladder, collapsing the gallbladder by applying a vacuum, eliminating the ring of tissue coupled to the gallbladder fundus by using a $CO_2$ laser or electrocoagulation, releasing the coupling of the cannula to the gallbladder fundus, and removing the cholecystoscopic cannula. The gallbladder disappears by means of atrophy.

The cholescystoscopic cannula—designed for coupling to the gallbladder fundus—comprises an inner tube, an outer tube slidable over the inner tube and containing a groove at the distal end of the inner wall of the outer tube, a first ring located proximate to the groove and fixed at the distal end of the outer tube, a second ring fixed to the distal end of the inner tube and slidable to contact the first ring of the outer tube and close the groove, a mechanical device to control the sliding between the inner and outer tubes, a first stopcock with an opening for the application of a vacuum between the inner and outer tubes, a second stopcock with a wide opening at the proximal end of the inner tube, which allows gas and fumes to escape from the lumen of the cholecystoscopic cannula, a hermetic rubber seal at a joint proximal contact point between the inner and outer tubes, and a removable safety catch located between the inner and outer tubes which prevents the inner tube from sliding and being advanced.

BRIEF DESCRIPTION OF THE DRAWINGS

Other features and advantages of the invention will be apparent from the following description taken in connection with the accompanying drawings, wherein:

FIG. 3A shows the electrocoagulation procedure of the cholecystoscopic gallbladder laser-sclerosis procedure according to the present invention.

FIG. 7A is a perspective view of the distal end of the cholecystoscopic cannula.

FIG. 7B is a perspective view of the cholecystoscopic cannula.

DETAILED DESCRIPTION OF THE PREFERRED EMBODIMENTS

Cholecystoscopic gallbladder laser-sclerosis procedure

Figure 1A:
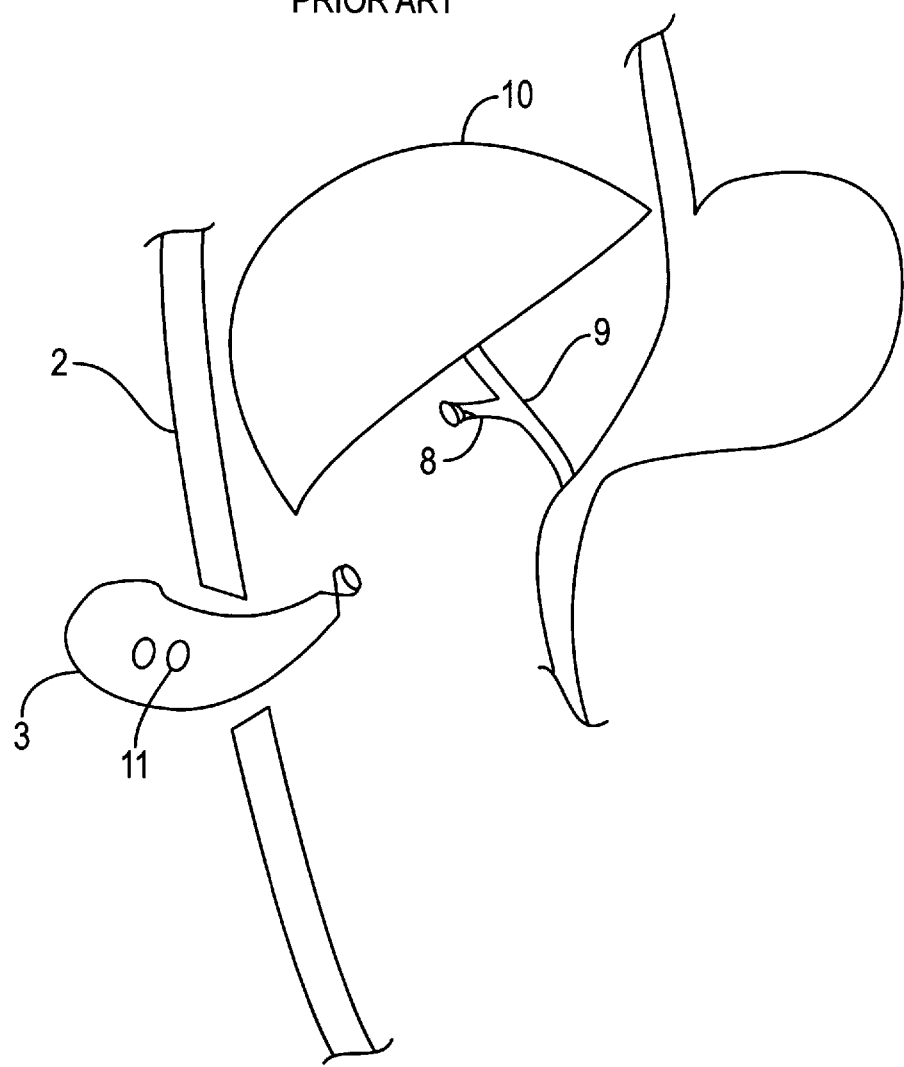
FIG. 1A shows a cholecystectomy as presently performed.
Figure 1B:
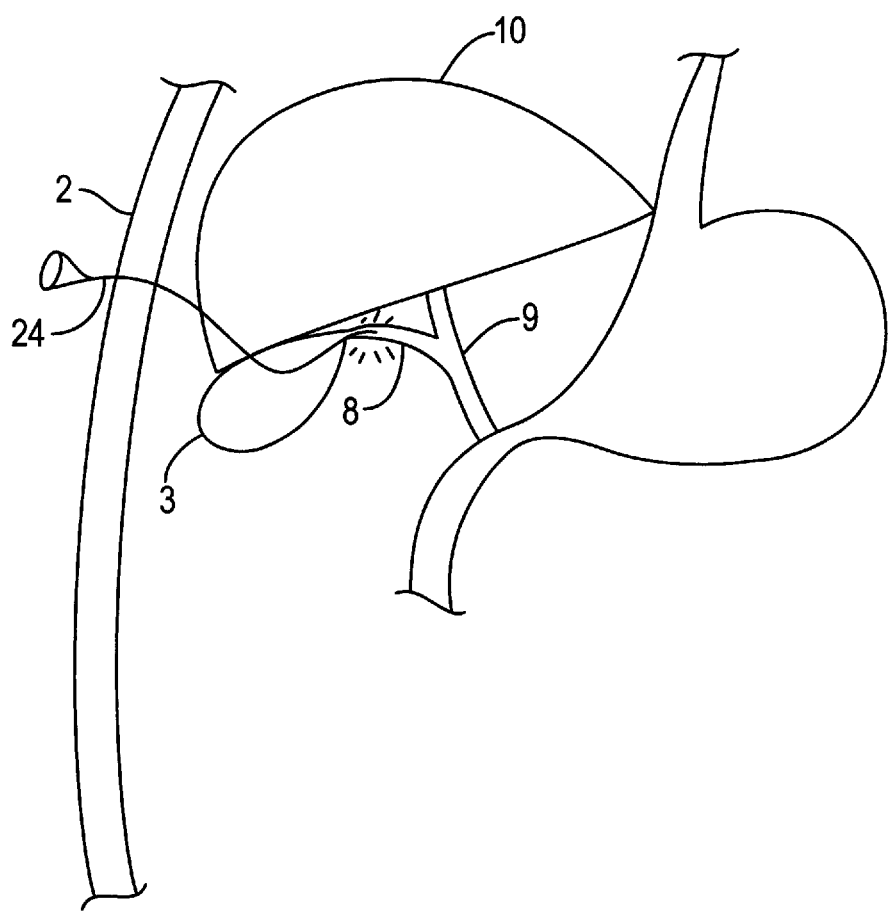
FIG. 1B shows a percutaneous radioscopic gallbladder chemical-sclerosis as presently performed.
Figure 2A:
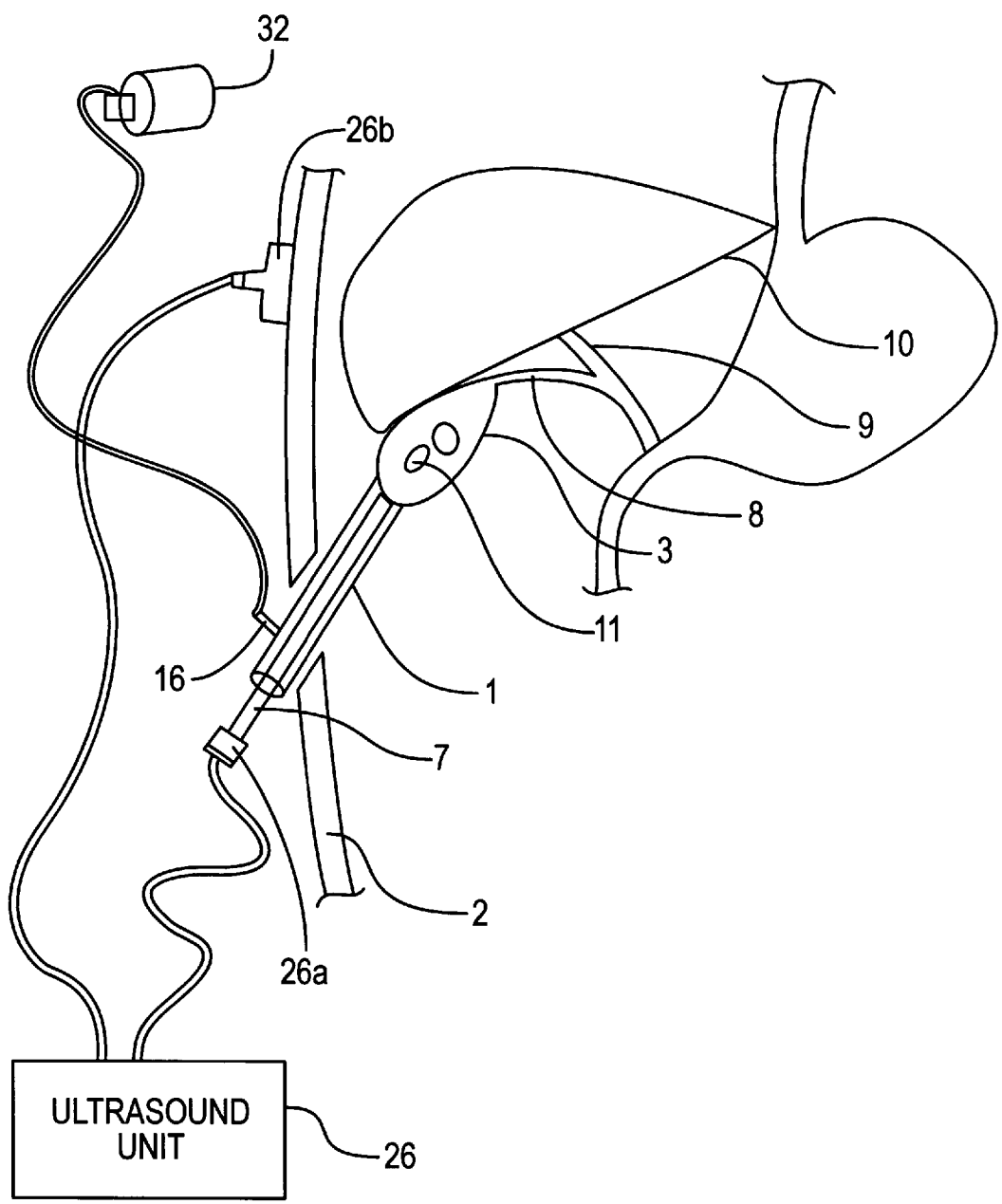
FIG. 2A shows the ultrasound procedure of the cholecystoscopic gallbladder laser-sclerosis procedure according to the present invention.
Figure 2B:
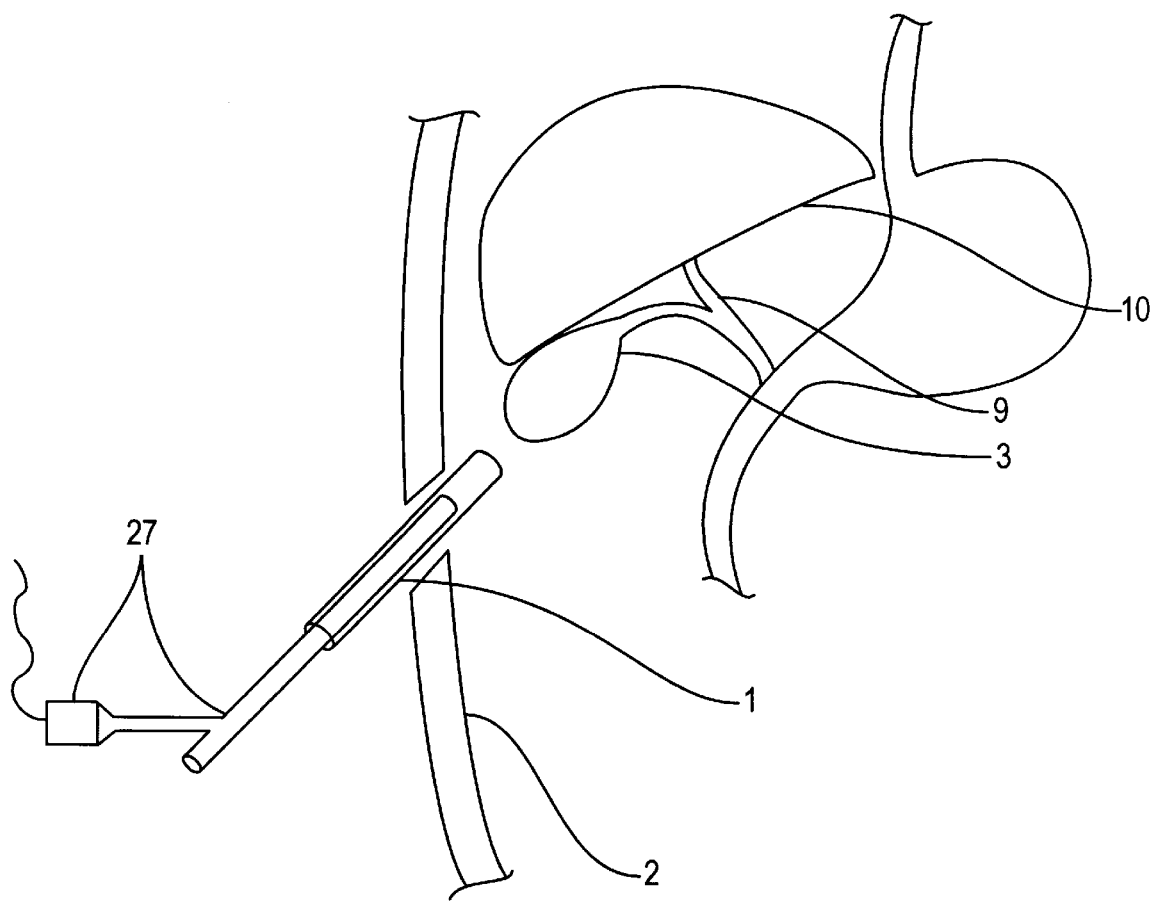
FIG. 2B shows the videoendoscope guiding the cholecystoscopic cannula toward the gallbladder fundus from within its lumen.
Figure 2C:
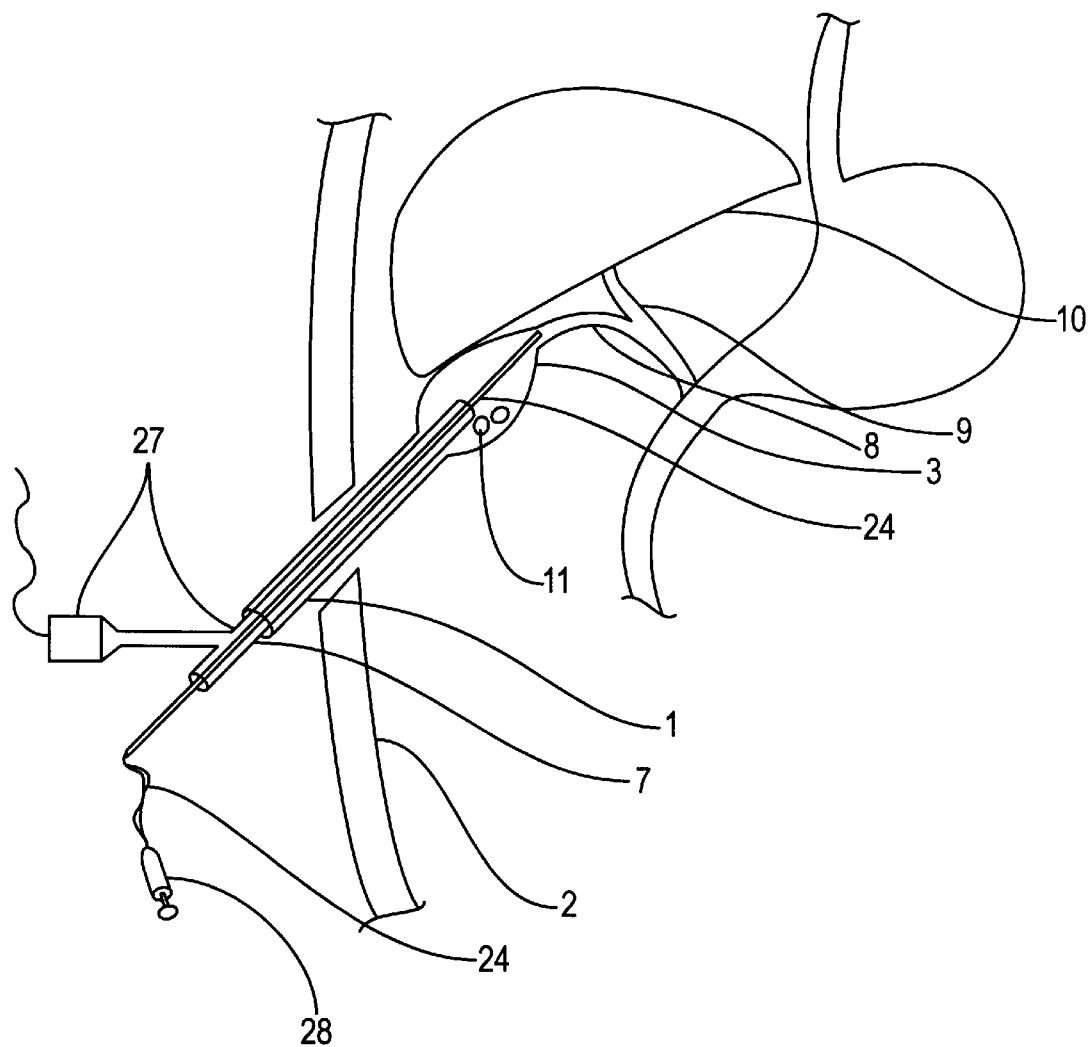
FIG. 2C shows the injection of contrast medium for the cholangiography as part of the cholecystoscopic gallbladder laser-sclerosis procedure according to the present invention.
Figure 2D:
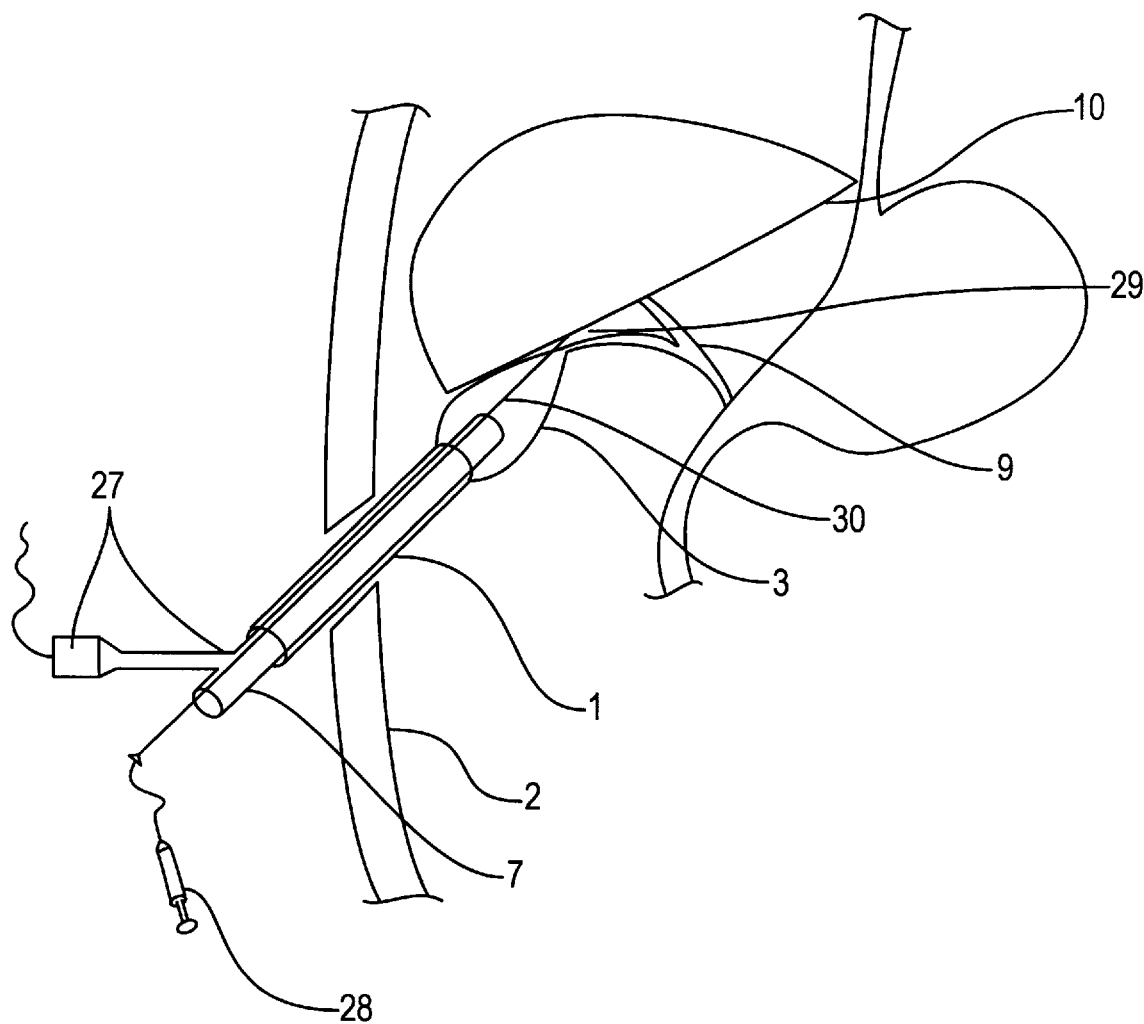
FIG. 2D shows the application of a local anesthetic to the peritoneal area between the gallbladder and the liver (or mesocyst), as part of the cholecystoscopic gallbladder laser-sclerosis procedure according to the present invention.
Figure 3B:
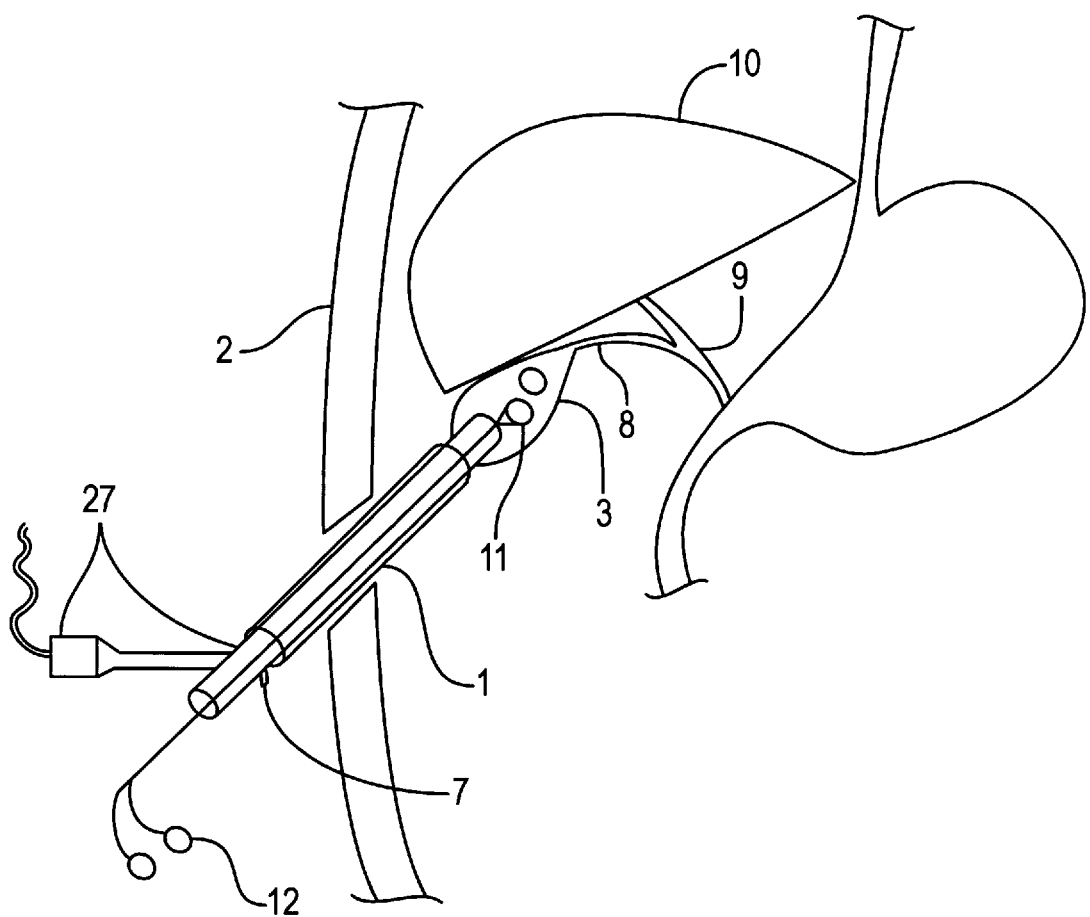
FIG. 3B shows the removal of the gallstones as part of the cholecystoscopic gallbladder laser-sclerosis procedure according to the present invention.

The present invention relates to a cholecystoscopic gallbladder laser-sclerosis procedure, as shown schematically in FIGS. 2A–2D, 3A, 3B, and 4A–4H, and utilizes a specially designed cannula, referred to as a cholecystoscopic cannula 1, to combine both the advantages of a single session cholecystectomy procedure, and a procedure which requires only a local anesthesia, such as the percutaneous radioscopic gallbladder chemical-sclerosis procedure. A description of the procedure follows.

A small incision is made in the abdominal wall 2 with conventional instruments and under local anesthesia. The site of the incision is chosen with regard to the location of the gallbladder 3 using Ultrasound 26. The specially-designed tube or cannula 1 (referred to as a cholecystoscopic cannula 1 and shown schematically in FIG. 2A) is placed through the incision and guided toward the gallbladder 3 fundus, without using hypertensive pneumoperitoneum. The guidance is performed by using either a videoendoscope 27 (see FIG. 2B) inside the cannula 1 where the advancing tip of the cannula 1 can be visualized, or by Ultrasound 26, where an internal probe 26a inside the cannula 1 and/or an external probe 26b on the abdomen helps guide the cannula 1 (see FIG. 2A). In addition, Ultrasound 26 is used to ensure that the cannula 1 has contacted the gallbladder 3 and not another organ, by allowing the internal probe 26a inside the cannula 1 to touch the gallbladder 3 itself, and the external probe 26b to visualize the cannula 1 contacting the gallbladder 3 and moving the gallbladder 3 (see FIG. 2A).

Once the cannula 1 has been guided to the gallbladder 3 fundus, the cannula 1 is coupled to the gallbladder 3 fundus by the following method. The inner side of the wall of the outer tube 4 of the cannula 1 has a groove 5 at its distal end into which a ring of gallbladder tissue 6 is forced to enter by means of suction. The groove 5 then closes (as will be discussed in detail below in connection with FIGS. 5–7B) and the gallbladder tissue 6 is trapped mechanically (see FIGS. 4A and 4B), thereby firmly coupling the cannula 1 to the gallbladder 3 fundus.

An endoscope 7 (see FIG. 2C) with an instrumentation channel is used to perforate the gallbladder 3 wall in the center of the trapped tissue ring 6 (see FIGS. 4A–4B) and enters into the gallbladder 3. There is no risk of damage to other organs because the groove 5 is in the inner side of the wall of the outer tube 4 of the cannula 1 and the entire maneuver can be performed under visual control using the endoscope 7 (see FIG. 2B). Therefore, the cannula-gallbladder coupling (see FIGS. 4A–4D) results in an effective, safe and hermetic maneuver with no risk of bile or gas leakage.

The next procedure performed is an endoscopy of the gallbladder 3 (not of the abdomen), or a cholecystoscopy (not a laparotomy), where the operation takes place inside the gallbladder 3 with a soft, low pressure insufflation like a gastroscopy or a colonoscopy, without using general anesthesia. The following steps in the procedure are performed using an endoscope 7 with one or two instrumentation channels placed inside the gallbladder 3 through the cholecystoscopic cannula 1.

The bile is first removed by means of suction, and a catheter is placed in the cystic duct 8 meatus (the opening where the cystic duct 8 begins). (The cystic duct 8 is the exit duct from the gallbladder 3 which communicates between the gallbladder 3 and the main duct 9) (see FIG. 2C). Contrast medium is injected through the catheter 24 using a syringe 28, and an intraoperative cholangiography is performed to evaluate the cystic duct 8 and the main biliary tree (see FIG. 2C). The mesocyst 29 or peritoneum attaching the liver 10 to the gallbladder 3 is infiltrated with local anesthesia by a puncture using a needle 30 inserted from within the gallbladder 3 to block the nerves running to the gallbladder 3 and prevent the patient feeling pain (see FIG. 2D). The cystic duct 8 meatus is closed with forceps 31 and then a high frequency electrocoagulation is applied (monopolar or preferably bipolar), sealing the cystic duct 8 walls one against the other, so that the cystic duct 8 meatus is closed in only one surgical session (see FIG. 3A).

The cystic duct 8 meatus can be grasped and pulled inside the gallbladder 3 lumen prior to the electrocoagulation to avoid injuries to other organs. If necessary, two instruments can be used, one for pulling the cystic duct 8 meatus and another one for grasping it. Both can be used through a double instrumentation channel endoscope 7 or through a wide single instrumentation channel endoscope 7.

The stones 11 are removed with instruments through the instrumentation channel endoscope 7. If 5 the stones 11 are large or numerous, they can be broken mechanically with a lithotritor forceps 12 and the fragments can be removed by means of a water stream and aspiration (see FIG. 3B).

The gallbladder 3 mucous membrane (the inner layer of the gallbladder 3 wall) is ablated by physical means. This produces enough damage to the tissue to require only one session for ablation to be completed. In contrast, chemical ablation requires multiple sessions.

Figure 4A:
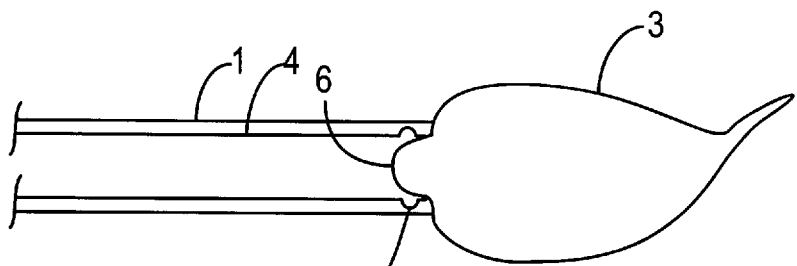
FIG. 4A shows a schematic cross-sectional view of the cholecystoscopic cannula of the present invention contacting the gallbladder fundus.
Figure 4B:
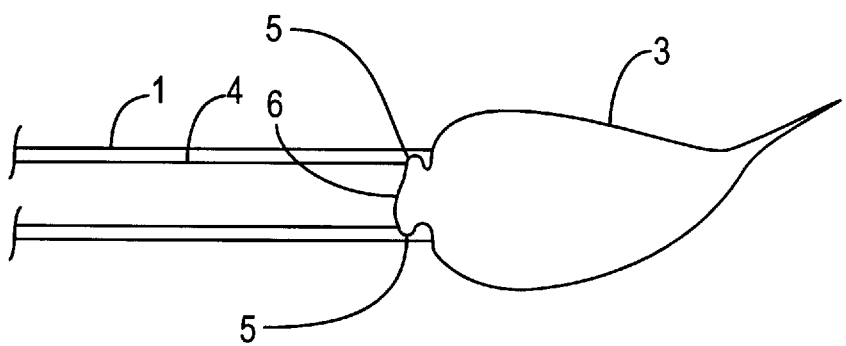
FIG. 4B shows how gallbladder tissue is forced to enter the groove in the distal end of the cholecystoscopic cannula by means of a vacuum.
Figure 4C:
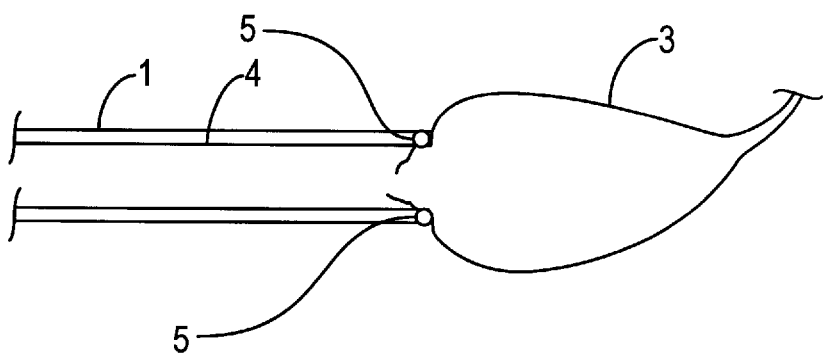
FIG. 4C shows how the groove at the distal end of the cholecystoscopic cannula is closed and the gallbladder tissue is trapped mechanically. The gallbladder wall has been perforated in the middle of the trapped gallbladder tissue ring.
Figure 4D:
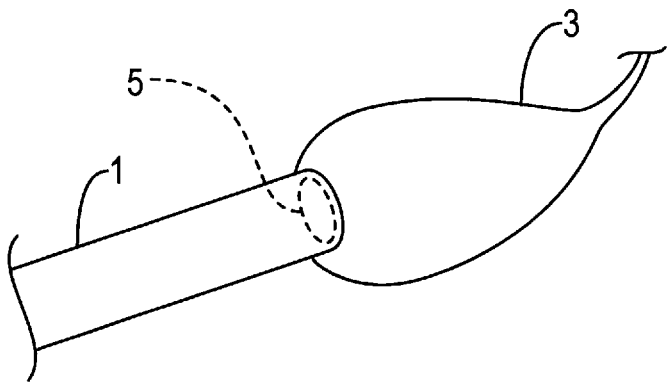
FIG. 4D is a perspective view showing the cholecystoscopic cannula contacting the gallbladder fundus. The dotted line represents the groove at the distal end of the cholecystoscopic cannula used in the coupling mechanism.
Figure 4E:
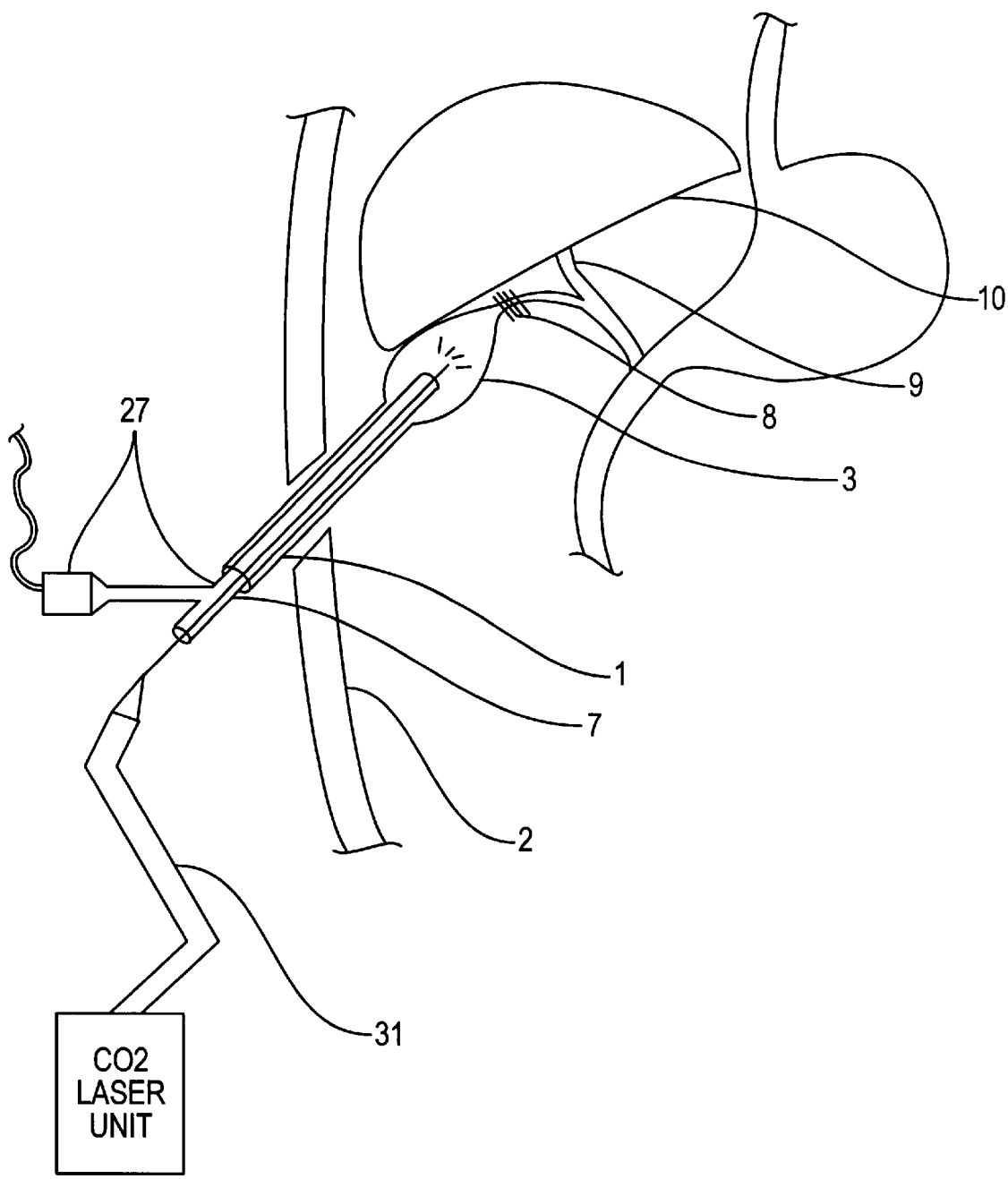
FIG. 4E shows the CO2 laser procedure of the cholecystoscopic gallbladder laser-sclerosis procedure according to the present invention.

The preferable physical means is the CO2 Laser 31 because it eliminates surface tissue, layer by layer, under strict visual control, without risk of gallbladder 3 perforation, as the CO2 laser 31 does not have the power to penetrate into the gallbladder 3 tissue (see FIG. 4E). Other physical means such as electrocoagulation at high frequency, cryocoagulation or boiling liquids, are less suitable. A laser also has the advantage of sealing blood vessels and biliaries and eliminating bacterial contamination.

Figure 4F:
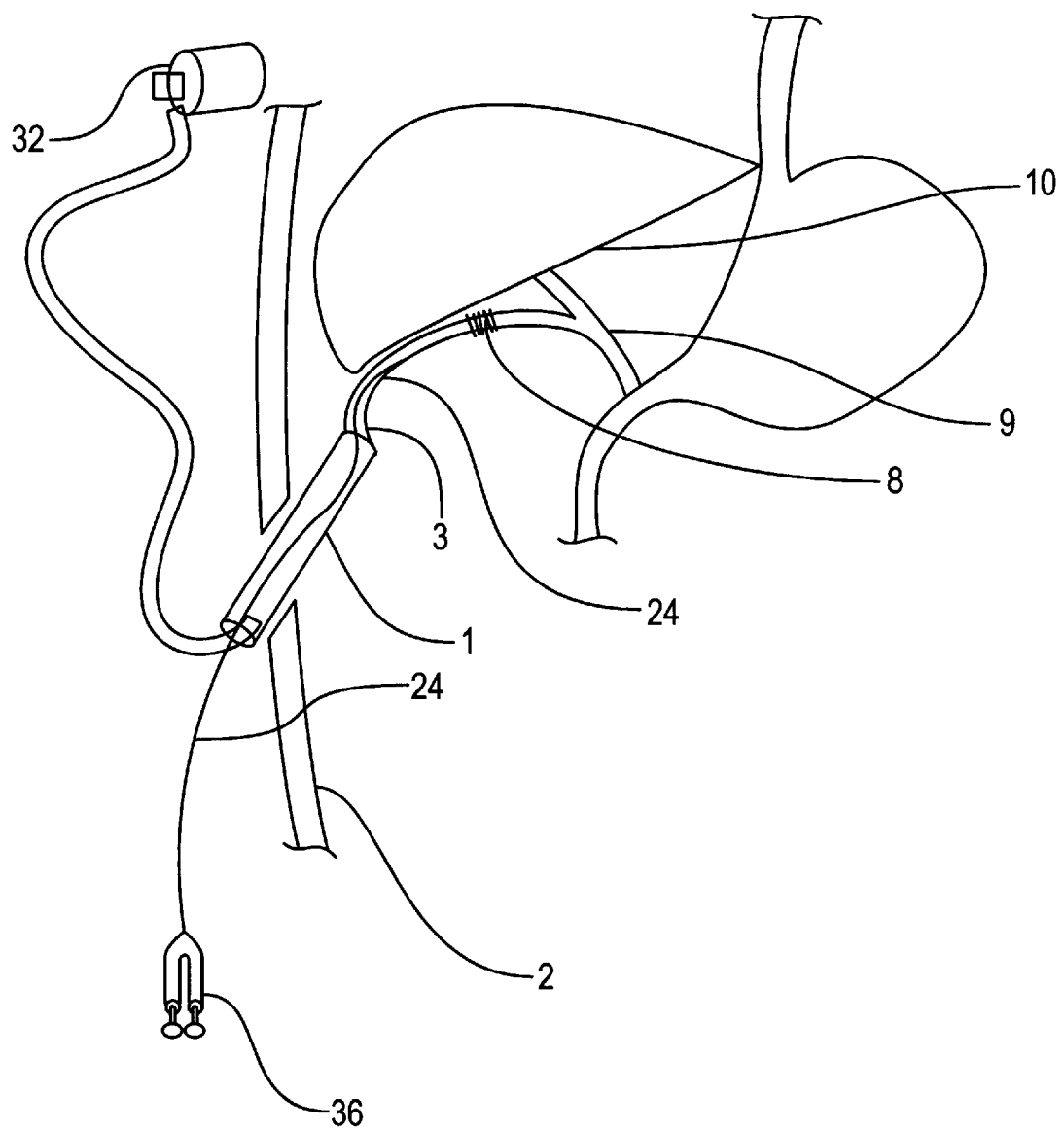
FIG. 4F shows the injection of the biological cement as part of the cholecystoscopic gallbladder laser-sclerosis procedure according to the present invention.

A biological cement is injected inside the gallbladder 3 via a special syringe 36 and a vacuum is applied, so that the gallbladder 3 collapses and its walls adhere one against the other (see FIG. 4F). This step attempts to generate a rapid intraluminal scar, which is conducive to gallbladder 3 scleroatrophy, and to avoid intraluminal liquid formation.

Figure 4G:
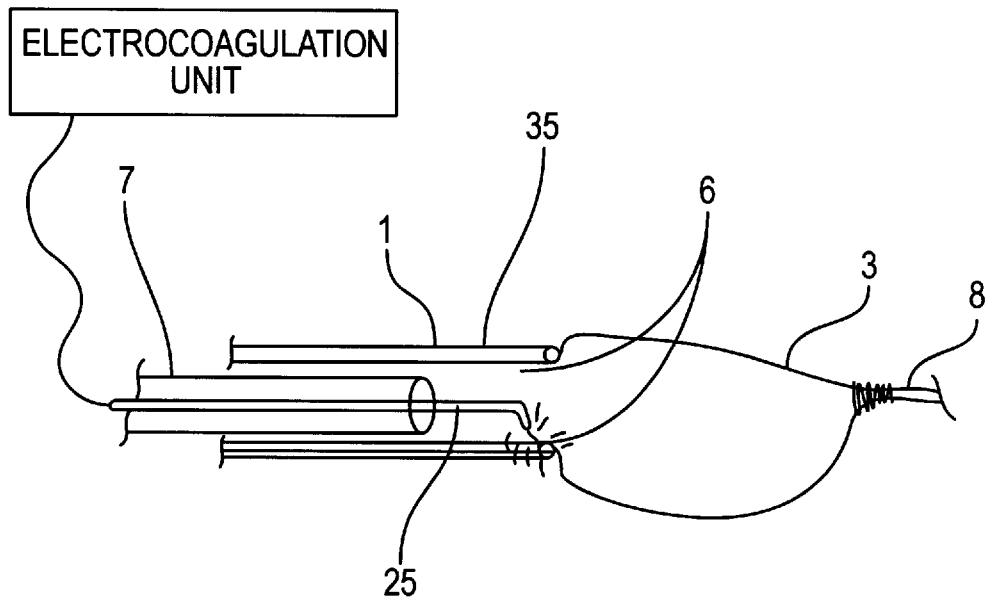
FIG. 4G shows application of monopolar electrocoagulation to the gallbladder tissue as part of the cholecystoscopic gallbladder laser-sclerosis procedure according to the present invention.
Figure 4H:
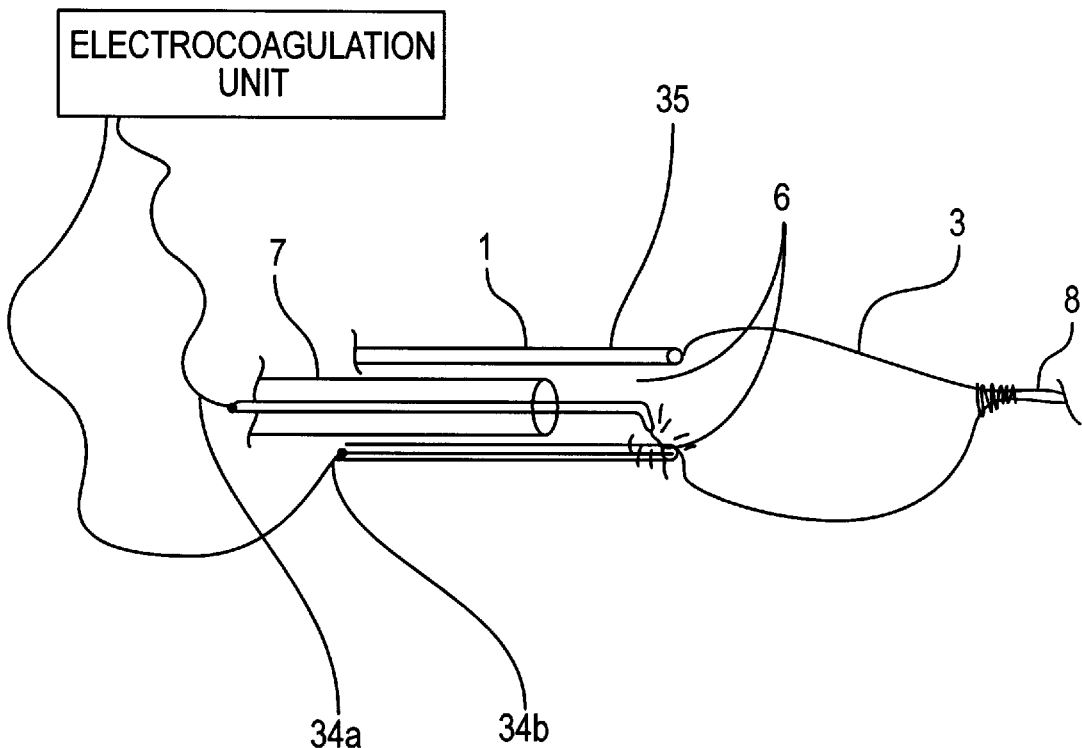
FIG. 4H shows application of bipolar electrocoagulation to the gallbladder tissue as part of the cholecystoscopic gallbladder laser-sclerosis procedure according to the present invention.
Figure 5:
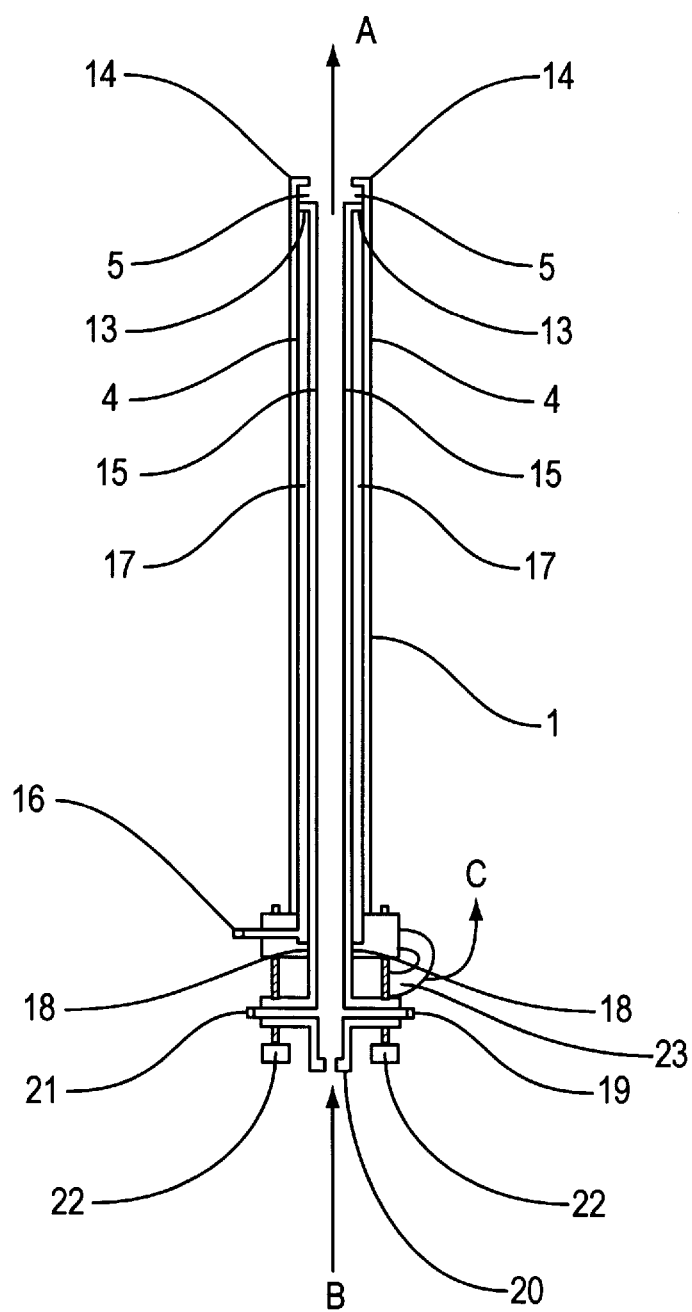
FIG. 5 shows a sectional view of the cholecystoscopic cannula.
Figure 6A:
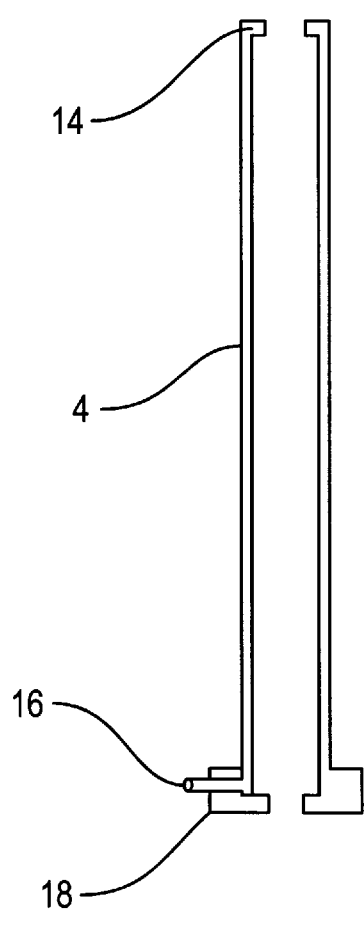
FIG. 6A shows the outer tube of the cholecystoscopic cannula.
Figure 6B:
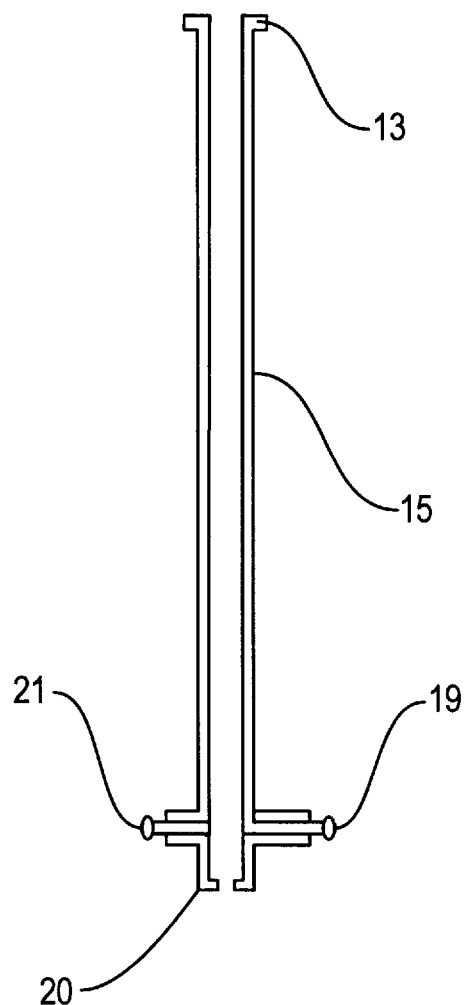
FIG. 6B shows the inner tube of the cholecystoscopic cannula.

The gallbladder tissue 6 trapped in the cannula groove 5 (see FIG. 5) can be eliminated with a CO2 laser 31 and also by using monopolar electrocoagulation by placing an electrode 25 through the instrumentation channel of the endoscope 7 (see FIG. 4G). Bipolar electrocoagulation can be used as well, wherein one pole 34*a* with an electrode is placed through the instrumentation channel of the endoscope 7 and the other pole 34*b* is located in the cannula 1 (see FIG. 4H).

The coupling system of the ring of gallbladder tissue 6 within the groove 5 of the distal end of the cannula 1 (see FIGS. 4A and 4B) is then released and the cholecystoscopic cannula 1 is withdrawn. A drainage tube is left either inside or outside the gallbladder 3, and the abdominal wall 2 incision is sutured. The gallbladder 3 disappears by means of atrophy.

Cholecystoscopic cannula

The cholecystoscopic cannula 1 comprises a tube which is placed through a small incision in the abdominal wall 2, guided toward the gallbladder 3 fundus (see FIGS. 2A–2H) and coupled to the gallbladder 3 fundus. As shown in more detail in FIGS. 5–7B, the cholecystoscopic cannula 1 has a groove 5 in the distal end of the inner side of the wall of the outer tube 4 of the cannula 1. Suction is used to force the gallbladder tissue 6 (see FIGS. 2A–4D).to enter into the groove 5 and then a ring 13 on the distal end of an inner tube 15 is advanced (in direction of the arrow A) to touch the ring 14 at the distal end of the outer tube 4, closing the groove 5 and trapping the gallbladder tissue 6.

More specifically, the cannula 1 has a double wall (or double tube) comprising the outer tube 4 and the inner tube 15, wherein each tube can slide with respect to the other. At the proximal end of the cannula 1 there is an opening with a stopcock 16 for connection with a flexible tube leading to a vacuum pump 32. The vacuum enters through the opening toward the space 17 between the outer tube 4 and the inner tube 15 and arrives at the groove 5 because the ring 13 is fenestrated (pierced with many openings). The contact points between the outer wall of the inner tube 15 and the inner wall of the outer tube 4 are at the distal end of the ring 13, which is fixed to the inner tube 15 and slidably contacts the outer tube 4. The ring 14 is fixed at the distal end of the outer tube 4. At the proximal end of the cannula 1, a joint 18 allows the outer tube 4 and the inner tube 15 to slide with respect to each other, and has a hermetic rubber seal 33 to avoid loss of vacuum.

At the proximal end of the cannula 1 there is a small opening with a stopcock 19 entering into the lumen of the inner tube 15 of the cannula 1, which allows insufflation of the gallbladder 3 (see FIGS. 4A–4D) through the cannula 1 lumen. The entrance opening 20 of the cannula 1 has a rubber seal (not shown), so it is possible to insufflate the gallbladder 3 (see FIGS. 4A–4D) from the stopcock opening 19 through the cannula 1 lumen (in the direction of arrow A) without a loss of gas from around the endoscope 7, which is placed in the direction of arrow B. At the proximal end of the cannula, there is disposed another opening with a wide stopcock 21, to allow gas or fumes to escape from the lumen. When the inner tube 15 slides within the outer tube 4, and the ring 13 advances and touches the ring 14, the gallbladder tissue 6 is trapped, then a mechanical device formed by a pair of screws 22 can be advanced, fixing both the outer tube 4 and the inner tube 15 in that position. By withdrawing the screws 22, both the outer tube 4 and the inner tube 15 are free to slide and the ring 13 can be withdrawn, thereby releasing the gallbladder tissue 6.

A safety catch 23 is disposed between the bases of both the outer tube 4 and the inner tube 15 and prevents the inner tube 15 from sliding, keeping both tubes withdrawn, and the groove 5 open. The safety catch 23 must be removed (in the direction of arrow C) prior to the advance of the inner tube 15 in order to activate the mechanical gallbladder tissue 6 trapping system. The cannula 1 has an external insulating layer 35 (see FIGS. 4G and 4H) to avoid the escape of current from high frequency electrocoagulation, if used during the operation.

It is contemplated that numerous modifications may be made to the procedure and the cannula of the invention without departing from the spirit and scope of the invention as defined in the following claims.

What is claimed is:

1. A cholecystoscopic surgical procedure for elimination of a gallbladder in a human patient, comprising the following steps:

inserting a cholecystoscopic cannula through a small incision in an abdominal wall of the human patient;

guiding said cholecystoscopic cannula toward a gallbladder fundus of the human patient and coupling said cholecystoscopic cannula to said gallbladder fundus by grasping a ring of tissue of said gallbladder fundus;

performing an operative endoscopy inside said gallbladder;

closing and sealing of a cystic duct meatus after performing said operative endoscopy;

removing gallstones from said gallbladder;

ablating a mucous membrane of said gallbladder by a first physical means;

injecting a biological cement into said gallbladder and collapsing said gallbladder;

eliminating said ring of tissue from said gallbladder fundus which is coupled to said cannula by using a second physical means; and releasing said coupling of said cholecystoscopic cannula to said gallbladder fundus and removing said cholecystoscopic cannula.

2. A cholecystoscopic surgical procedure according to claim 1, wherein the step of guiding said cholecystoscopic cannula toward said gallbladder fundus further comprises using a videoendoscope inside said cholecystoscopic cannula.

3. A cholecystoscopic surgical procedure according to claim 1, wherein the step of guiding said cholecystoscopic cannula toward said gallbladder fundus further comprises using an ultrasound.

4. A cholecystoscopic surgical procedure according to claim 3, wherein said ultrasound uses at least one of an external probe and an internal probe.

5. A cholecystoscopic surgical procedure according to claim 1, wherein the step of coupling said cholecystoscopic cannula to said gallbladder fundus further comprises forcing said ring of tissue of said gallbladder fundus into a groove at a distal end of said cannula.

6. A cholecystoscopic surgical procedure according to claim 5, wherein said ring of tissue of said gallbladder fundus is forced into said groove in said cholecystoscopic cannula by application of a vacuum.

7. A cholecystoscopic surgical procedure according to claim 1, wherein said surgical procedure is performed under local anesthesia.

8. A cholecystoscopic surgical procedure according to claim 1, wherein said surgical procedure is performed under general anesthesia.

9. A cholecystoscopic surgical procedure according to claim 1, wherein the step of performing said operative endoscopy inside said gallbladder further comprises:

perforating a wall of said gallbladder using an endoscope and entering said gallbladder;

applying a soft, low pressure insufflation to said gallbladder;

removing bile by using a vacuum;

placing a catheter in a cystic duct meatus;

injecting contrast medium into said gallbladder; and performing an intraoperative cholangiography.

10. A cholecystoscopic surgical procedure according to claim 9, wherein said operative endoscopy is performed under a local anesthetic applied to a peritoneal area between said gallbladder and said liver of the human patient.

11. A cholecystoscopic surgical procedure according to claim 1, wherein the closing of said cystic duct meatus is performed using a forceps.

12. A cholecystoscopic surgical procedure according to claim 1, wherein the sealing of said cystic duct meatus is performed using electrocoagulation.

13. A cholecystoscopic surgical procedure according to claim 12, wherein said electrocoagulation is performed using monopolar electrocoagulation.

14. A cholecystoscopic surgical procedure according to claim 12, wherein said electrocoagulation is performed using bipolar electrocoagulation.

15. A cholecystoscopic surgical procedure according to claim 1, wherein removing said gallstones from said gallbladder is performed using a lithotritor forceps.

16. A cholecystoscopic surgical procedure according to claim 1, wherein the step of ablating said mucous membrane of said gallbladder by said first physical means includes a CO2 laser.

17. A cholecystoscopic surgical procedure according to claim 1, wherein the step of eliminating said ring of tissue from said gallbladder fundus which is coupled to said cannula by using said second physical means includes a CO2 laser.

18. A cholecystoscopic surgical procedure according to claim 1, wherein the step of eliminating said ring of tissue from said gallbladder fundus which is coupled to said cannula by using said second physical means includes electrocoagulation.

19. A cholecystoscopic surgical procedure according to claim 18, wherein said electrocoagulation further comprises the step of placing a first electrode through an operating channel of said endoscope to achieve a monopolar electrocoagulation.

20. A cholecystoscopic surgical procedure according to claim 19, wherein said electrocoagulation further comprises the step of placing a second electrode in said cholecystoscopic cannula to achieve a bipolar electrocoagulation.

21. A cholecystoscopic surgical procedure according to claim 1, wherein the step of collapsing said gallbladder after the injection of the biological cement is performed using a vacuum.

22. A cholecystoscopic surgical procedure for elimination of a gallbladder in a human patient, comprising the following steps:

inserting a cholecystoscopic cannula through a small incision in an abdominal wall of the patient;

guiding said cholecystoscopic cannula toward a gallbladder fundus of the human patient;

coupling said cholecystoscopic cannula to said gallbladder fundus by forcing a ring of tissue of said gallbladder fundus into a groove at a distal end of said cannula by applying a vacuum;

perforating a gallbladder wall at said gallbladder fundus and performing an operative endoscopy inside said gallbladder;

closing of a cystic duct meatus using a forceps and sealing of said cystic duct meatus by electrocoagulation;

removing gallstones from said gallbladder using a lithotritor forceps;

ablating a mucous membrane of said gallbladder by a first physical means;

injecting a biological cement into said gallbladder;

collapsing said gallbladder by applying a vacuum;

eliminating said ring of tissue from said gallbladder fundus which is coupled to said cannula by using a second physical means; and releasing said coupling of said cholecystoscopic cannula of a remnant of gallbladder tissue and removing said cholecystoscopic cannula from the abdominal wall of the human patient.

23. A cholecystoscopic surgical procedure according to claim 22, wherein the step of guiding said cholecystoscopic cannula toward said gallbladder fundus further comprises using a videoendoscope inside said cholecystoscopic cannula.

24. A cholecystoscopic surgical procedure according to claim 22, wherein the step of guiding said cholecystoscopic cannula toward said gallbladder fundus further comprises using an ultrasound.

25. A cholecystoscopic surgical procedure according to claim 24, wherein said ultrasound uses at least one of an external probe and an internal probe.

26. A cholecystoscopic surgical procedure according to claim 22, wherein said surgical procedure is performed under local anesthesia.

27. A cholecystoscopic surgical procedure according to claim 22, wherein said surgical procedure is performed under general anesthesia.

28. A cholecystoscopic surgical procedure according to claim 22, wherein the step of performing said operative endoscopy inside said gallbladder further comprises:

perforating a wall of said gallbladder using an endoscope and entering said gallbladder;

applying a soft, low pressure insufflation to said gallbladder;

removing bile by using a vacuum;

placing a catheter in a cystic duct meatus;

injecting contrast medium into said gallbladder; and performing an intraoperative cholangiography.

29. A cholecystoscopic surgical procedure according to claim 22, wherein said electrocoagulation is performed using monopolar electrocoagulation.

30. A cholecystoscopic surgical procedure according to claim 22, wherein said electrocoagulation is performed using bipolar electrocoagulation.

31. A cholecystoscopic surgical procedure according to claim 22, wherein the step of ablating said mucous membrane of said gallbladder by said first physical means includes a CO2 laser.

32. A cholecystoscopic surgical procedure according to claim 22, wherein the step of eliminating said ring of tissue from said gallbladder fundus which is coupled to said cannula by using said second physical means includes a CO2 laser.

33. A cholecystoscopic surgical procedure according to claim 22, wherein the step of eliminating said ring of tissue from said gallbladder fundus which is coupled to said cannula by using said second physical means includes electrocoagulation.

34. A cholecystoscopic surgical procedure according to claim 33, wherein said electrocoagulation further comprises the step of placing a first electrode through an operating channel of said endoscope to achieve a monopolar electrocoagulation.

35. A cholecystoscopic surgical procedure according to claim 34, wherein said electrocoagulation further comprises the step of placing a second electrode in said cholecystoscopic cannula to achieve a bipolar electrocoagulation.

* * * * *